US008625738B2

(12) United States Patent
Boyd et al.

(10) Patent No.: US 8,625,738 B2
(45) Date of Patent: Jan. 7, 2014

(54) RADIATION THERAPY AND SCANNING SYSTEM

(75) Inventors: Douglas Perry Boyd, Las Vegas, NV (US); Samuel Moon-Ho Song, Las Vegas, NV (US)

(73) Assignee: Telesecurity Sciences, Inc., Las Vegas, NV (US)

( * ) Notice: Subject to any disclaimer, the term of this patent is extended or adjusted under 35 U.S.C. 154(b) by 455 days.

(21) Appl. No.: 12/564,652

(22) Filed: Sep. 22, 2009

(65) Prior Publication Data

US 2010/0166144 A1 Jul. 1, 2010

Related U.S. Application Data

(60) Provisional application No. 61/099,044, filed on Sep. 22, 2008.

(51) Int. Cl.
*A61N 5/10* (2006.01)
(52) U.S. Cl.
USPC ............................................ 378/65; 378/98.8
(58) Field of Classification Search
USPC ........... 378/65, 189, 10, 12, 98.8; 250/370.09
See application file for complete search history.

(56) References Cited

U.S. PATENT DOCUMENTS

| 4,352,021 A * | 9/1982 | Boyd et al. ........................ 378/12 |
| 5,197,088 A * | 3/1993 | Vincent et al. .................... 378/10 |
| 2005/0047548 A1 * | 3/2005 | Sengupta et al. .............. 378/137 |
| 2006/0072849 A1 | 4/2006 | Marc |
| 2007/0206722 A1 * | 9/2007 | Hoffman et al. ................. 378/19 |
| 2008/0037707 A1 * | 2/2008 | Rothschild et al. ............. 378/57 |
| 2008/0205597 A1 | 8/2008 | Ono |
| 2008/0205599 A1 | 8/2008 | Hashimoto |
| 2009/0034683 A1 * | 2/2009 | Tamakoshi ...................... 378/91 |
| 2010/0014638 A1 * | 1/2010 | Oreper et al. .................... 378/65 |

FOREIGN PATENT DOCUMENTS

WO    WO 2006101231 A1 *  9/2006

OTHER PUBLICATIONS

U.S. Appl. No. 12/274,067, filed Nov. 19, 2008, Method and Apparatus for Production and Maintenance of Electron Beam Space-Charge Neutralization, (26) pages.

* cited by examiner

*Primary Examiner* — Glen Kao
(74) *Attorney, Agent, or Firm* — The Small Patent Law Group; Dean D. Small

(57) ABSTRACT

A radiation therapy and scanning system is provided. The radiation and therapy scanning system includes a therapy source adapted to deliver a predetermined dose of treatment radiation along an axis to a patient positioned in a scan field, a stationary scanning source producing an electron beam, and a detector positioned to partially circumscribe the scan field. The radiation therapy and scanning system also includes a target arranged concentric with the detector and located opposite the detector across the scan field, the target positioned at an angle θ to the axis such that when the electron beam impinges on the target the target transmits radiation through the scan field to the detector.

19 Claims, 9 Drawing Sheets

# RADIATION THERAPY AND SCANNING SYSTEM

This application claims the benefit of U.S. Provisional Application No. 61/099,044, filed Sep. 22, 2008, the subject matter of which is herein incorporated by reference in its entirety.

BACKGROUND OF THE INVENTION

This invention relates generally to scanning electron beam scanners and more particularly to a method and apparatus for electron beam scanning.

Conventional scanning electron beam scanners, such as those used in computed tomography (CT) imaging systems, produce cross-sectional and three-dimensional (3D) images of the human body and objects such as baggage and cargo. The conventional scanning electron beam scanner includes a radiation source that is axially aligned with both a target and a detector. During operation, the radiation source emits radiation that impinges on the target. In response to this impingement, the target generates x-rays that are directed through the patient or object to the detector.

Moreover, conventional radiation therapy devices are often used to generate a high energy beam. The generated beam is typically axially aligned with the patient to receive the radiation treatment. More specifically, the conventional radiation therapy device includes a gantry which can be swiveled around a horizontal axis of rotation in the course of a therapeutic treatment. A treatment head ("collimator") can be set at any angle (rotation on the z axis) of gantry directs a radiation beam along an axis toward a patient. The radiation beam is typically generated by a linear accelerator positioned within gantry. The radiation beam is trained on a treatment zone of the patient. The treatment zone is an area which includes the tumor for example to be treated.

It would be desirable to incorporate a conventional electron beam scanner into a system having a radiation therapy source. However, since the conventional therapy source is axially aligned with the treatment area, and the radiation source used in the conventional scanning electron beam scanner is axially aligned with both the target and the detector, the conventional scanning electron beam scanner cannot easily be incorporated into a conventional radiation therapy system.

BRIEF DESCRIPTION OF THE INVENTION

In one embodiment, a radiation therapy and scanning system is provided. The radiation and therapy scanning system includes a therapy source adapted to deliver a predetermined dose of treatment radiation along an axis to a patient positioned in a scan field, a stationary scanning source producing an electron beam, and a detector positioned to partially circumscribe the scan field. The radiation therapy and scanning system also includes a target arranged concentric with the detector and located opposite the detector across the scan field, the target positioned at an angle θ to the axis such that when the electron beam impinges on the target the target transmits radiation through the scan field to the detector.

In another embodiment, a detector for an electron beam scanner is provided. The detector includes a substrate having a first side and a second opposing side, a pixel array formed on the substrate first side, and an x-ray shield formed on the substrate opposing side.

In a further aspect, a detector for an electron beam scanner is provided. The detector includes a detector positioned to partially circumscribe a scan field, the detector divided into a pair of detector rings arranged adjacent to one another and separated by a gap extending at least partially about a circumference of the detector, and an x-ray shield extending at least partially through the gap.

DETAILED DESCRIPTION OF THE INVENTION

Figure 1:
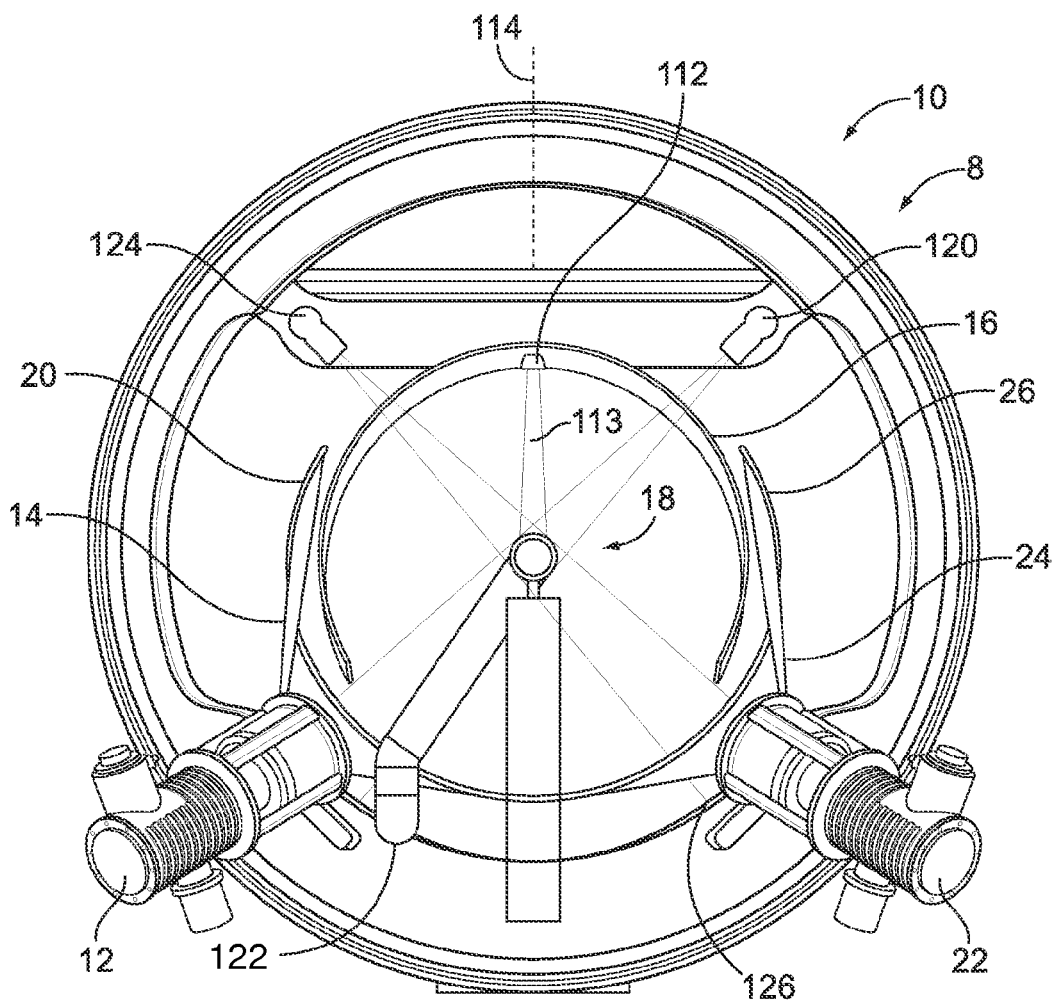
FIG. 1 is an end view of an exemplary therapy and scanning system in accordance with an embodiment of the present invention.
Figure 10:
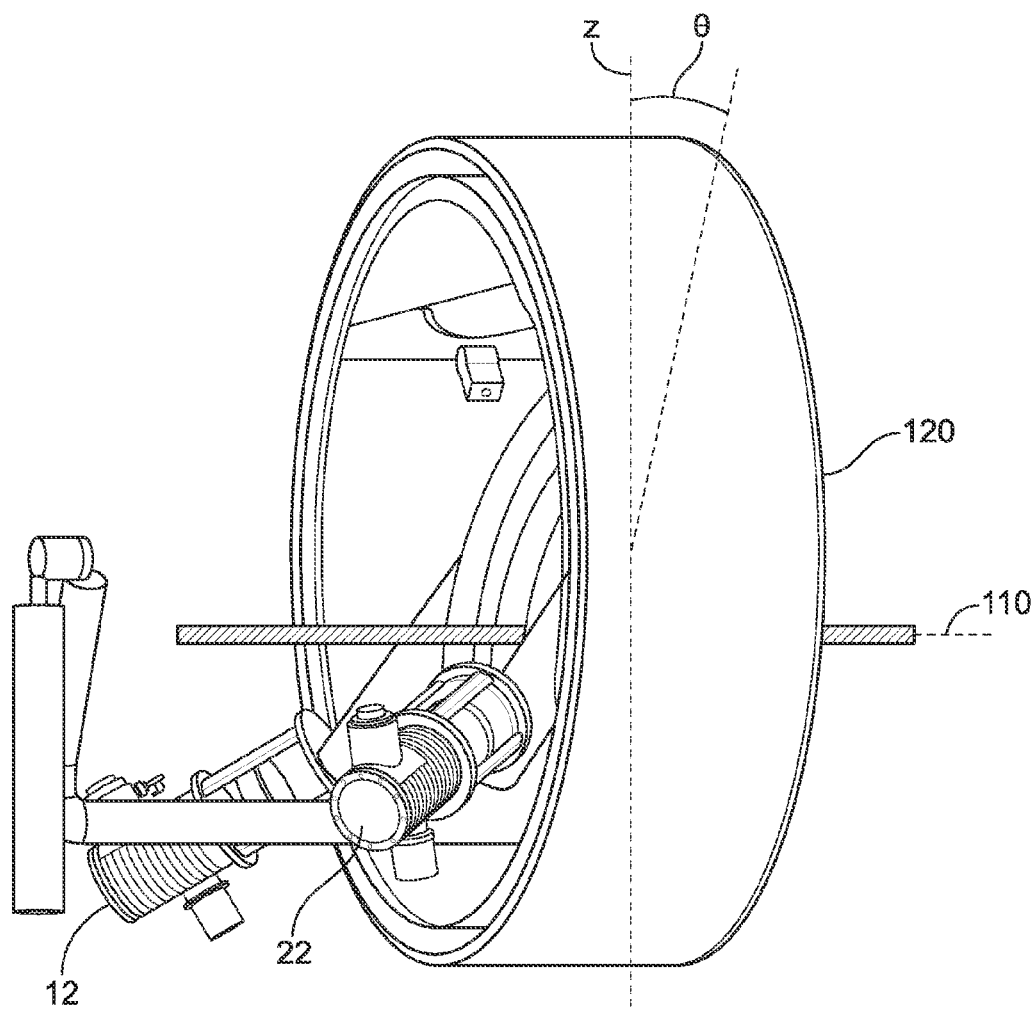
FIG. 10 is a side perspective view of the therapy and scanning system shown in FIG. 1 in accordance with an embodiment of the present invention.
Figure 11:
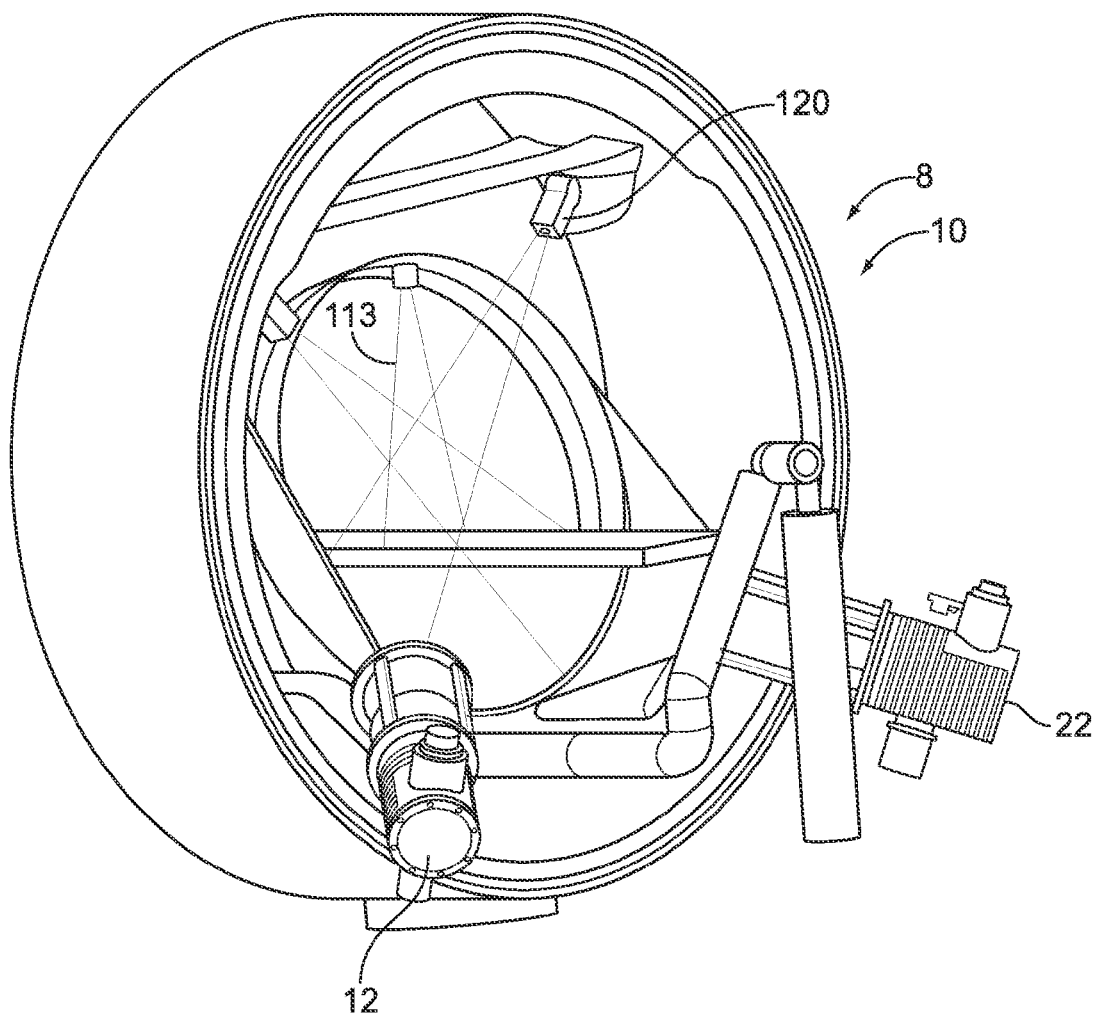
FIG. 11 is another side perspective view of the therapy and scanning system shown in FIG. 1 in accordance with an embodiment of the present invention.

FIG. 1 is an end view of an exemplary scanning and therapy system 8 installed in an exemplary system in accordance with an embodiment of the present invention. FIG. 10 is a side perspective view of the scanning and therapy system 8 shown in FIG. 1. FIG. 11 is another side perspective view of the scanning and therapy system 8 shown in FIG. 1. In the exemplary embodiment, the therapy and scanning system 8 includes a gantry 110 which can be swiveled around a horizontal axis of rotation 110 in the course of a therapeutic treatment. A treatment head 112 directs a radiation beam 113 along axis 114 toward a patient (not shown). The radiation beam 113 is generated by a linear accelerator positioned within gantry 110. The radiation beam 113 may be a form of high energy radiation. The radiation beam 113 is trained on a treatment zone of the patient. The treatment zone is an area which includes the area to be treated such as a tumor for example. To facilitate aligning the treatment head 112 onto the treatment zone, the scanning and therapy system also includes a therapy source positioning system that is adapted to provide a signal to facilitate locating the therapy beam on the treatment zone. The therapy source positioning system includes a first x-ray source 120 that projects an x-ray beam onto a first detector 122. The therapy and scanning system 10 also includes a second x-ray source 124 that projects an x-ray beam onto a second detector 126. In the exemplary embodiment, the therapy source 112, x-ray radiation sources 120 and 124, and the detectors 122 and 126 form a therapy system that is incorporated into the scanning and therapy system 10.

During operation, the outputs from the two x-ray detectors 122 and 126 are used to triangulate the position of the therapy source 112. More specifically, to ensure that the therapy source is properly aligned with the lesion, etc. that is to be radiated, the combination of the radiation sources 120 and 124 and the detectors 122 and 126 are used to accurately position the therapy source 112. As shown in FIGS. 1, 10, and 11, the therapy source 112, the radiation sources 120 and 124, and the detectors 122 and 126 are all positioned at the same axial location along the Z axis.

As shown in FIG. 1, the scanning and therapy system 8 also includes an electron beam scanner 10. The electron beam scanner 10 includes a stationary source 12 (e.g. an electron gun) producing an electron beam 14. The electron beam scanner 10 also includes a detector 16 that is positioned to partially circumscribe a scan field 18. The electron beam scanner 10 includes the electron gun 12 and also includes a target 20 that is arranged concentric with the detector 16 and located opposite the detector 16 across the scan field 18. In the exemplary embodiment, the electron beam scanner 10 also includes a second electron gun 22 producing a second electron beam 24, and a second target 26 that is arranged concentric with the detector 16 and located opposite the detector 16 across the scan field 18.

As shown in FIGS. 1, 10, and 11, in the exemplary embodiment, the detector 16 is offset from the Z-axis by an angle θ. More specifically, as discussed above, the angle θ is sufficient to enable the radiation sources used in the scanning electron beam scanner 10 to be aligned with both the targets and the detectors while still maintaining the axial alignment of the radiation sources 120 and 124 with both the detectors 122 and 126 and the therapy source 112 used in the therapy portion of the system 8.

Figure 2A:
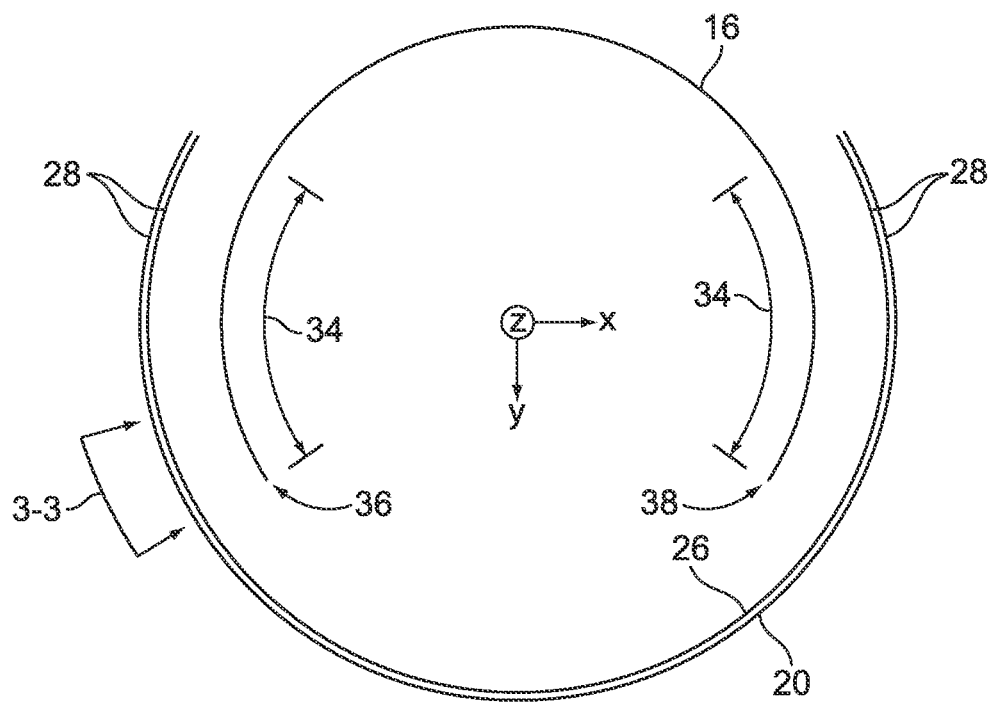
FIG. 2 is a simplified schematic diagram illustrating the physical relationship between the detector and the targets shown in FIG. 1 in accordance with an embodiment of the present invention.
Figure 2B:
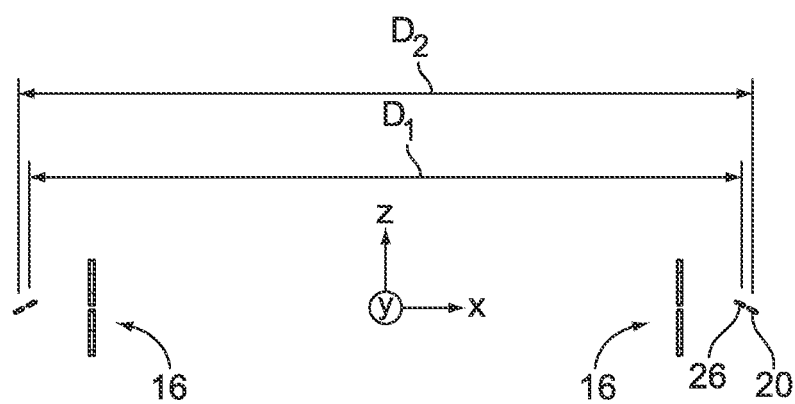

FIG. 2A is a simplified schematic diagram illustrating the physical relationship between the detector 16, the target 20, and the target 26 shown in FIG. 1 in accordance with an embodiment of the present invention. FIG. 2B is a cross-section of the detector 16, target 20, and target 26 shown in FIG. 2A. As shown in FIG. 2A, each of the targets 20 and 26 have end portions 28 circumferentially overlapping the at least a portion of the detector 16. In one embodiment, shown in FIG. 2B, a diameter D1 of the target 20 is greater than a diameter D2 of the second target 26. Increasing the diameter of the second target 26 enables the electron beam 24 emitted from the second stationary source 22 to impinge on the second target 26 without contacting the first target 20. Optionally, the diameter of the target 20 may be less than the diameter of the second target 26 such that the electron beam 14 emitted from the stationary source 12 does not impinge on the second target 26.

Figure 3:
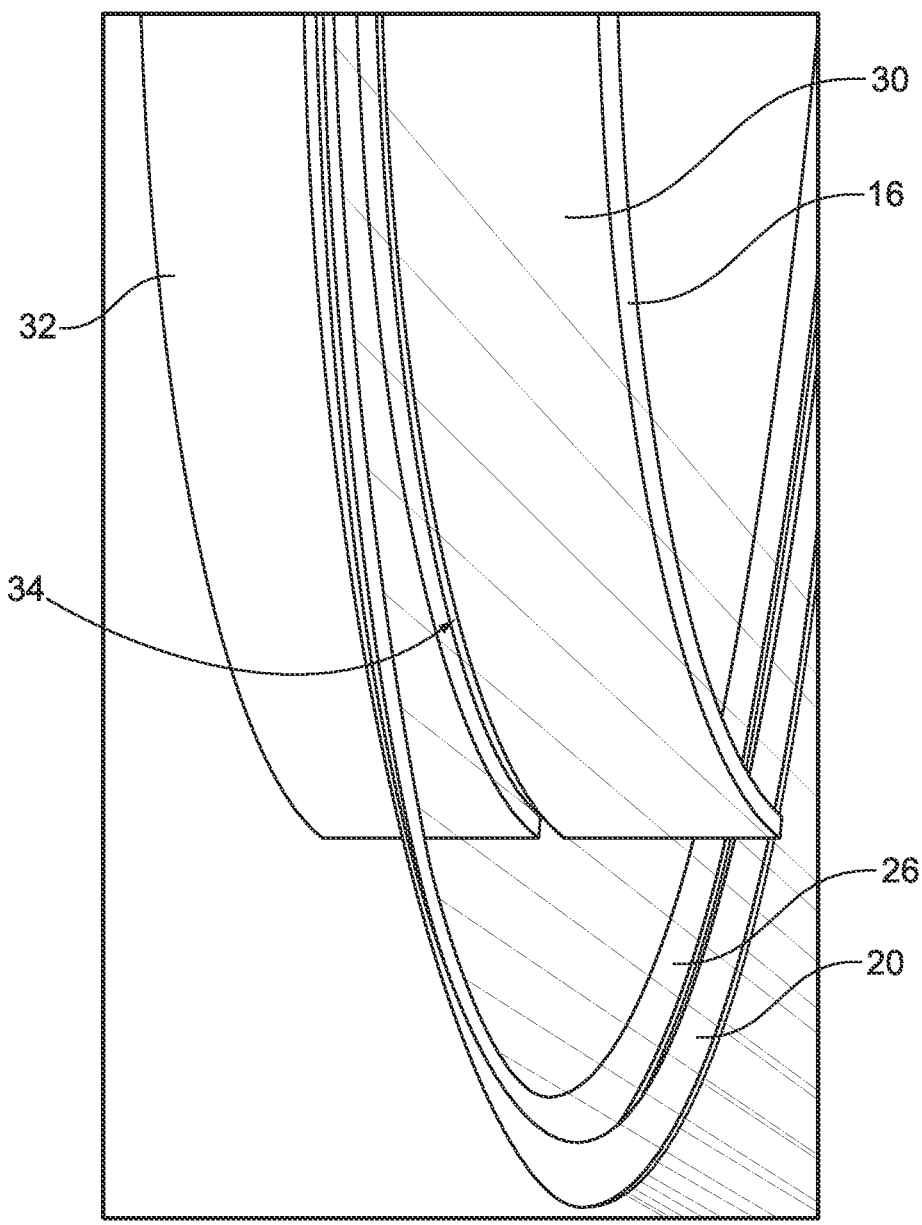
FIG. 3 is a sectional view of a portion of the electron beam scanner shown in FIG. 2 taken along lines 3-3 in accordance with an embodiment of the present invention.

FIG. 3 is a sectional view of a portion of the electron beam scanner 10 shown in FIG. 2 taken along lines 3-3. As shown in FIG. 3, the target 20 is positioned alongside and approximately parallel to target 26 along the Z-axis. In the exemplary embodiment, the detector 16 is divided into a pair of detector rings 30 and 32 that arranged adjacent to one another and separated by a gap 34 extending at least partially about a circumference of the detector 16. In the exemplary embodiment, each of the targets 20 and 26 are radially aligned with the gap 34 that is defined between the detector rings 30 and 32, such that when the electron beams, 14 and 24 respectively, impinge on their respective target 20 and 26, each target 20 and 26 transmits radiation through the gap 34 across the scan field 18 to an associated section of the detector, e.g. 30 and 32, respectively. As shown in FIG. 2, the detector 16 includes a first end 36 and a second end 38. In the exemplary embodiment, the gap 34 extends from the first end 36 at least partially towards the detector second end 38. Moreover, the gap 34 extends from the second end 38 at least partially towards the first end 36.

As discussed above, the first and second targets 20 and 26 have end portions 28 that circumferentially overlap the detector 16 and are radially aligned with the gap 34 between the detector rings 30 and 32 such that when the electron beams 14 and 24 produced by the first and second stationary sources, 12 and 22, impinge on their respective targets, 20 and 26, the first and second targets 20 and 26 each transmit radiation through the gap 34, across the scan field 28, to an associated section of the detector.

Figure 5:
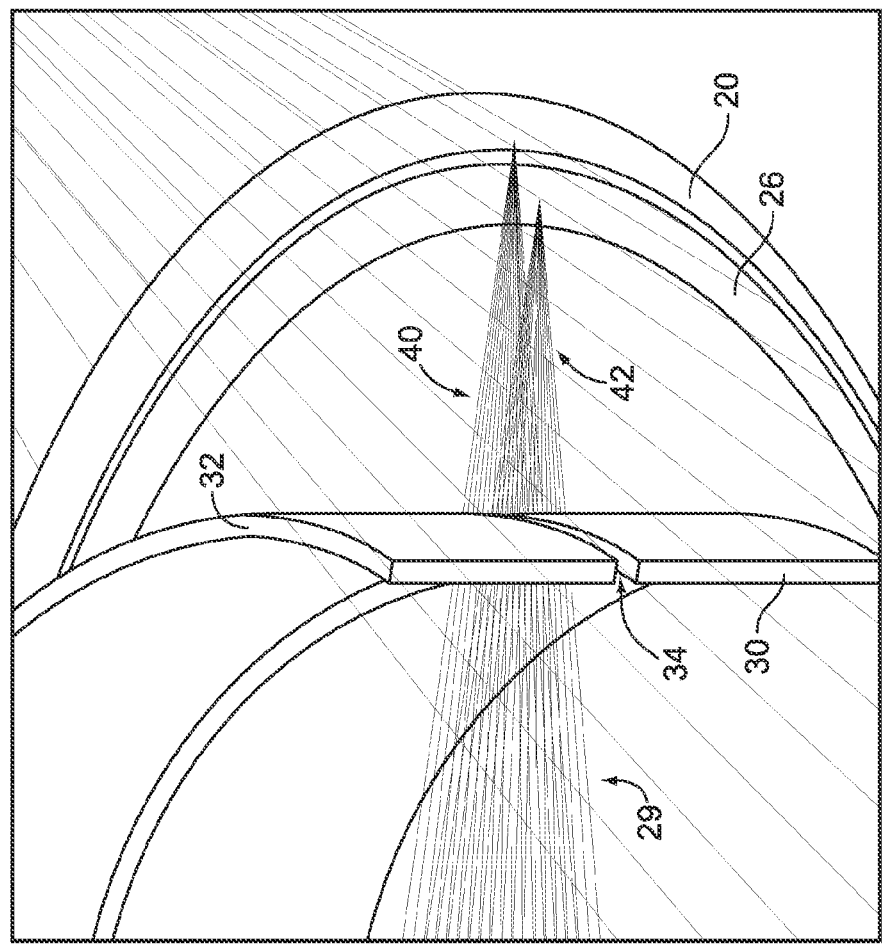
FIG. 5 illustrates a portion of the beam pattern shown in FIG. 4 in accordance with an embodiment of the present invention.
Figure 4:
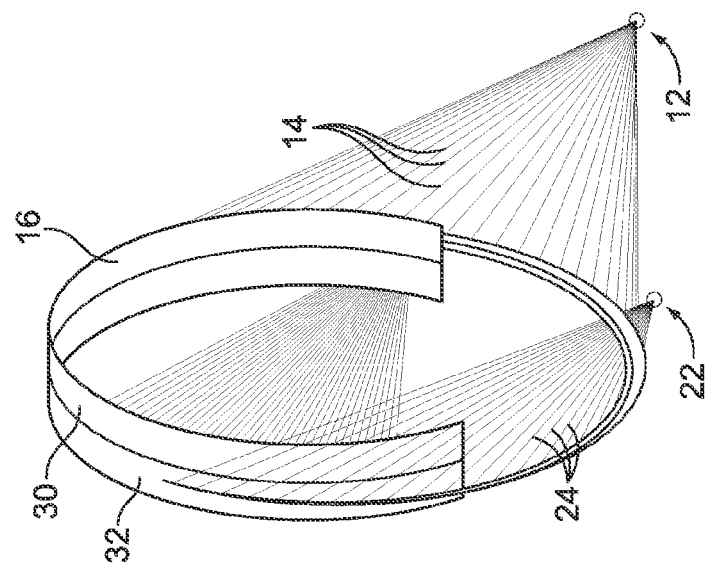
FIG. 4 illustrates an exemplary radiation pattern produced by the electron beam scanner shown in FIG. 1 in accordance with an embodiment of the present invention.

FIG. 4 illustrates an exemplary radiation pattern produced by the electron beam scanner 10 shown in FIG. 1. FIG. 5 illustrates a portion of the beam pattern shown in FIG. 4. In the exemplary embodiment, shown in FIGS. 4 and 5, each stationary source 12 and 22 may be embodied as an electron gun. A conventional electron gun produces an electron beam inside a highly evacuated chamber. The electron beam produced by the electron gun is transmitted to a target wherein the electron beam impinges on a target. The electron beam impinging on a tungsten target for example causes radiation to be emitted from the target. Since the electron gun produces a single electron beam, this electron beam is typically rastered along a surface of the target to produce x-rays. In the exemplary embodiment, a cone-shaped field of x-rays is produced by the single electron beam. This cone-shaped field of x-rays is then transmitted through an object to be imaged, to a detector, wherein a resultant image may be produced.

Referring again to FIGS. 4 and 5, in the exemplary embodiment, during operation the source 12 transmits a single electron beam 14 that impinges on the target 20 or 26. It should be realized that numerous electron beams 14 are illustrated to reflect the raster pattern that produced by the single source 12 on the target 20 or 26. The target 20 or 26 emits a fan or cone-shaped field of x-rays 40 that are transmitted through the gap 34, across the scan field 28, to the detector ring 30 or 32. Moreover, the second stationary source 22 transmits a second electron beam 24 that impinges on the second targets 20 or 26. Again, the target 20 or 26 emits a cone-shaped field of x-rays 42 that are transmitted through the gap 34, across the scan field 28, to the detector ring 30 or 32.

Figure 6:
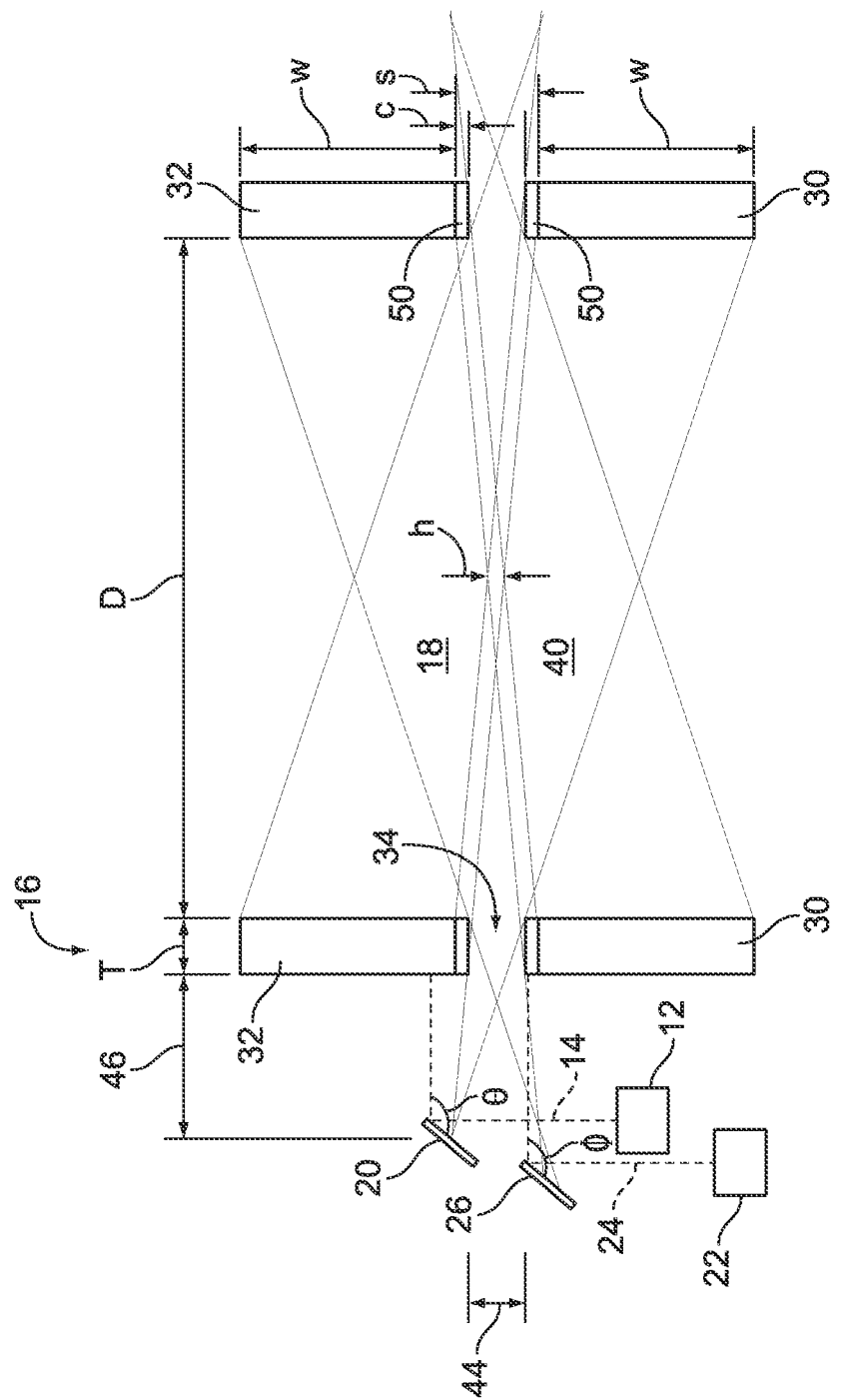
FIG. 6 is a simplified schematic illustration of a portion of the electron beam scanner shown in FIG. 1 in accordance with an embodiment of the present invention.

FIG. 6 is a simplified schematic illustration of a portion of the electron beam scanner 10 shown in FIG. 1. As discussed above, the source 12 transmits a single electron beam 14 that impinges on the target 20. The target 20 then emits a fan-shaped field of x-rays 40 that are transmitted through the gap 34. Moreover, the source 22 transmits a single electron beam 24 that impinges on the target the target 26. The target 26 then emits a fan-shaped field of x-rays 42 that are transmitted through the gap 34. In the exemplary embodiment, target 20 is disposed and an angle θ with respect to the detector 16 and target 26 is disposed at an angle Φ with respect to the detector 16. In one embodiment, the angle θ is equal to the angle Φ. Optionally, the angle θ is different than the angle Φ. In the exemplary embodiment, the angle θ and the angle Φ are approximately thirty-six degrees.

In the exemplary embodiment, both the angle θ and the angle Φ are preselected based on the geometry of the desired electron beam scanner 10. More specifically, the angle θ and the angle Φ are based on at least the width (W) of each detector ring 30 and 32, the distance (D) between the opposing portions of the same detector ring, the width 44 of the gap 34, and the distance between each respective target 20 and 26 and the detector 16. For example, if either of angles θ or Φ are increased to greater than thirty-six degrees to enable the electron beam scanner 10 to be assembled in a more compact arrangement, the distance 46 defined between the targets 20 or 26 is decreased. In the exemplary embodiment, the above parameters are selected such that the width of each field of x-rays 40 and 42 when impinging on a respective detector ring 30 and 32 is substantially the same as the width (W) of the detector ring itself. As such, if the width of either detector ring 30 or 32 is increased or increased, the width 44 of the gap 34 may be narrowed or widened to define a narrow or wider field of x-rays. Optionally, the distance 46 between the target 20 or 26 may be increased or decreased such that the resultant field of x-rays is narrower or wider when impinging on the detector rings 30 and 32.

As shown in FIG. 6, the gap 34 defined between the detector ring 30 and the detector ring 32 enables the field of x-rays 40 to overlap the field of x-rays 42 in the scan field 18. This overlap produces a diamond-shaped area (h) that is not imaged. In the exemplary embodiment, the area (h) is between 0 and approximately two millimeters in width. To improve image quality the area (h) is made to be very small, e.g. between approximately 0 millimeters and approximately 2 millimeters. In one exemplary embodiment, to reduce the area (h) and thus further improve image quality, a thickness (c) of an x-ray shield 50 is reduced. For example, as shown in FIG. 6, and discussed in more detail below, the detector ring 30 is separated from the detector ring 32 by a distance (S). Moreover, the detector 16 also includes an x-ray shield 50 that is coupled to the detector 16 and extends at least partially through the gap 34. As shown in FIG. 6, the area (h) is directly related to the thickness (c) of the x-ray shield 50. Accordingly, the area (h) may be reduced by reducing the thickness (c) of the x-ray shield 50. In the exemplary embodiment, the thickness (c) is greater than 0 millimeters and less than approximately 2 millimeters.

Figure 7:
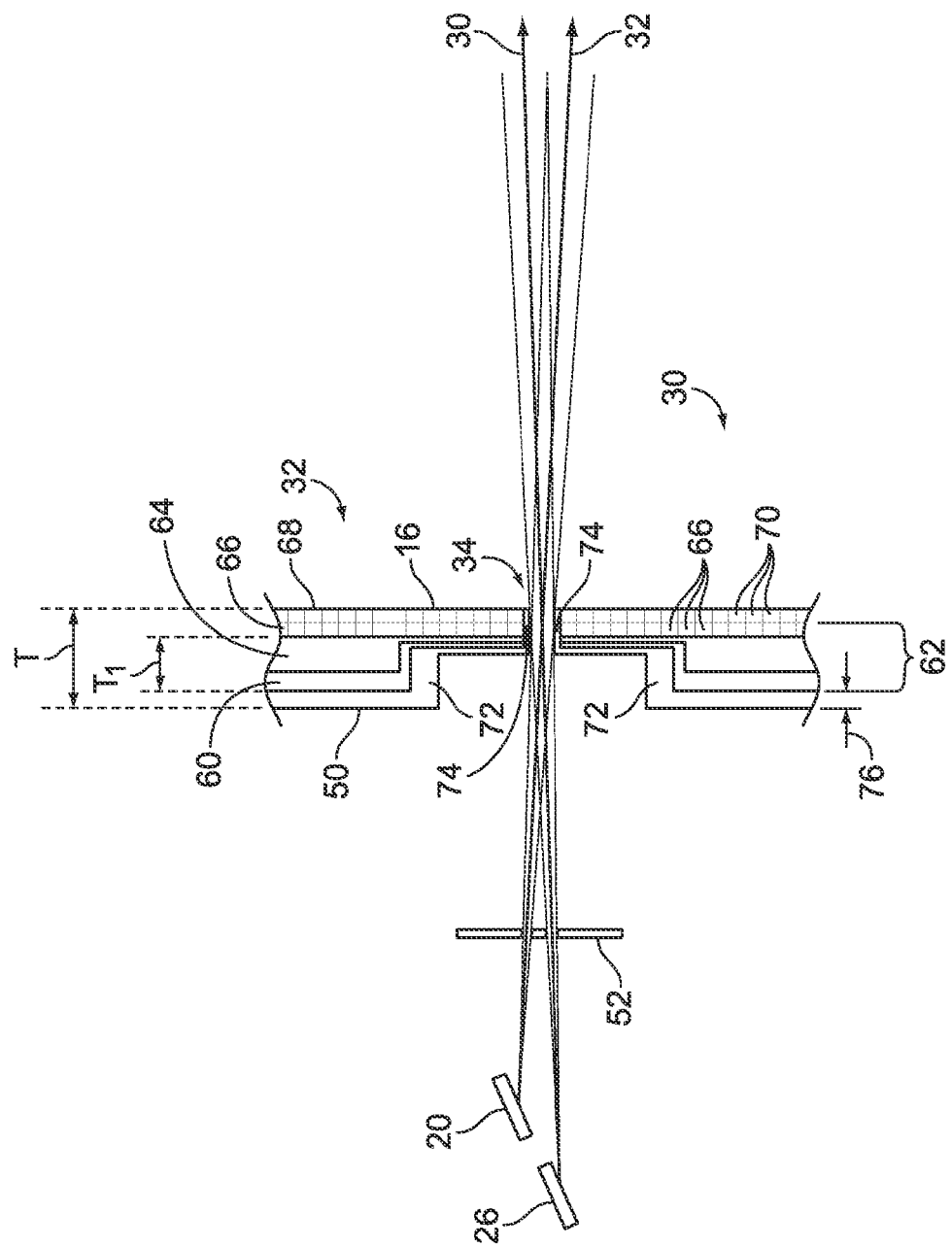
FIG. 7 is a cross-sectional view of the detector shown in FIG. 1 in accordance with an embodiment of the present invention.

FIG. 7 is a cross-sectional view of the detector 16 shown in FIG. 1. In the exemplary embodiment, the electron beam scanner 10 also includes a collimator 52 that is positioned between the targets 20 and 26 and the detector 16. During operation, the collimator 52 is adapted to narrow the field of x-rays 40 and/or 42 to focus the field of x-rays 40 and 42 through the gap 34. More specifically, the collimator 52 is adapted to narrow the spatial cross-section of the field of x-rays 40 and 42 and to align the field of x-rays 40 and 42 with the gap 34.

As discussed above, the detector 16 includes the detector ring 30 that is separated from the detector ring 30 by a gap 34. In the exemplary embodiment, the detector 16 is adapted for detecting x-rays emitted from the targets 20 and 26. In the exemplary embodiment, the detector 16 includes a substrate 60 and a pixel array 62 (sometimes referred to as a photosensor array) disposed on the substrate 60. The pixel array 62 includes a data acquisition electronics layer 64 and a plurality of photodiodes 66 arranged in rows and columns. The data acquisition electronics layer 64 includes a capacitor (not shown) and a switching device, such as a thin film transistor TFT (not shown). Each respective photodiode 66 is electrically coupled to a respective capacitor and switching device. The switching devices selectively couple a respective capacitor and photodiode to a respective data line (not shown). The detector 16 also includes a plurality of scan lines (not shown) for addressing a plurality of individual pixels. The detector 16 also includes a scintillator medium 68 disposed on the pixel array 64. In the exemplary embodiment, the scintillator medium 68 includes a plurality of scintillators 70, wherein a single scintillator 70 is disposed on each respective photodiode 66. In the exemplary embodiment, the detector 16 provides approximately 18 centimeters of coverage along the Z axis. More specifically, in the exemplary embodiment, each detector ring 30 and 32, includes a pixel array 62 having two rows of photodiodes 66 arranged in twenty-four columns. Moreover, each photodiode 66 is approximately 2 millimeters×3 millimeters. Accordingly, the total detector area is 48*(2 mm*3.5 mm)=18 centimeters.

During operation, x-rays emitted from the targets 20 and 26 are absorbed in the scintillators 70. Each scintillator 70 then generates optical photons which in turn pass into a photosensor, such as the photodiode 66. The photon is absorbed in the photosensor and an electrical signal corresponding to an incident photon flux is generated. The electrical signal is then transmitted, via the data lines, to a computer to generate an image of the scanned object.

In the exemplary embodiment, the detector 16 also includes the x-ray shield 50. As shown in FIG. 7, the x-ray shield 50 extends along the length of the detector 16. In the exemplary embodiment, the x-ray shield 50 is fabricated using a material that inhibits x-rays from passing through the material. For example, the x-ray shield may be fabricated using a lead material. The x-ray shield 50 includes a first shield portion 72 that extends along a length of the detector 16. The x-ray shield 50 also includes a second shield portion 74 that is perpendicular to the first shield portion 72. As shown in FIG. 7 the second shield portion 72 is adapted to be received within the gap 34. In the exemplary embodiment, the second shield portion 74 has an outer diameter or width that is approximately equal to the width (S) of the gap 34 as shown in FIG. 4. As discussed above, the thickness (c) of the second shield portion 74 may be either increased or decreased based on the geometry of the electron beam scanner. In the exemplary embodiment, a thickness 76 of the first shield portion 72 is selected based on the power of the x-rays being transmitted through the detector 16. During operation, the shield 50 is adapted to restrict x-rays from contacting any portion of the detector 16 with the exception of the scintillator medium 68. The shield 50 therefore protects the electronic components within the detector 16 from undesirable effects that may be introduced from the exposure to x-rays other than through the scintillator medium 68.

As shown in FIG. 7, the detector 16 may have a variable thickness. More specifically, a portion of the detector 16 may have the first thickness (T) and a second portion of the detector 16 may have a second thickness (T1). In the exemplary embodiment T<T1 to enable the width and or length of the gap 34 to be reduced. As discussed above, reducing the size of the gap 34 further improves image quality by reducing the size of the area (h) that is not imaged.

Figure 8:
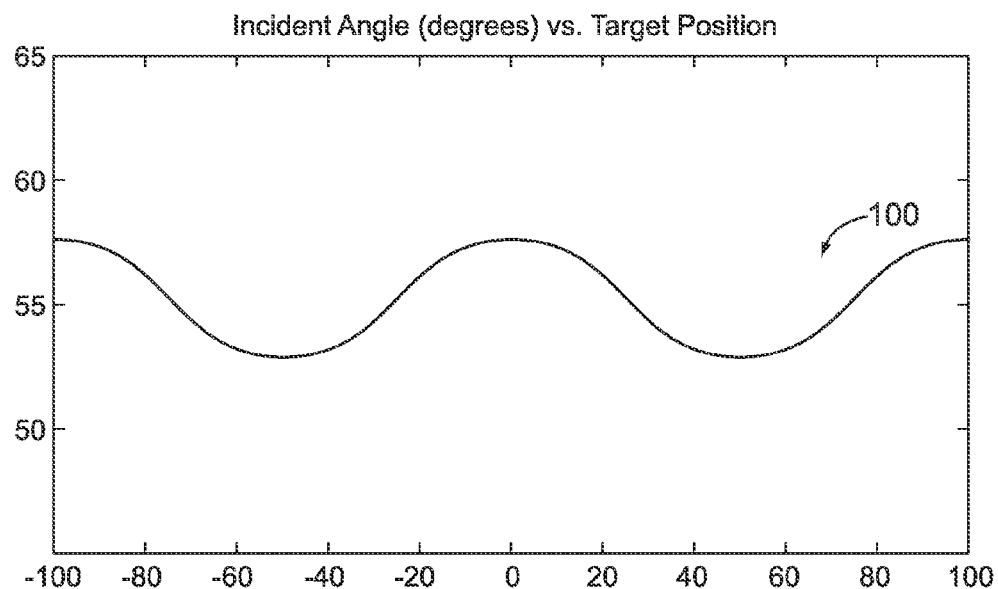
FIG. 8 is a graphical illustration of an exemplary incident angle of an exemplary electron beam impinging on an exemplary target in accordance with an embodiment of the present invention.

FIG. 8 is a graphical illustration of an exemplary incident angle 80 of at least one of the electron beams 14 or 24 impinging on a respective target 20 or 26. More specifically, FIG. 8 illustrates the incident angle 80 of the electron beam 20 or 26 with respect to the normal vector of either the target 20 or target 26. During operation when the electron beam impinges on the target, the electron beam does not impinge on the target transversely. In the exemplary embodiment, the incident angle 80 of the electron beam causes an electron beam having an oval-shaped cross-sectional profile to impinge on the target. For example, if the incident angle 80 is greater than 60 degrees, since the incident angle 80 is defined as 1/cos 60 degrees=½, the radius of the electron beam increases by a factor of 2. To maintain the radius of the electron beam to be as small as possible, in the exemplary embodiment, the incident angle 80 is less than 60 degrees. In the exemplary embodiment, as shown in FIG. 8, the incident angle 80 of the electron beam on a respective target is between approximately 52 and 58 degrees.

Figure 9:
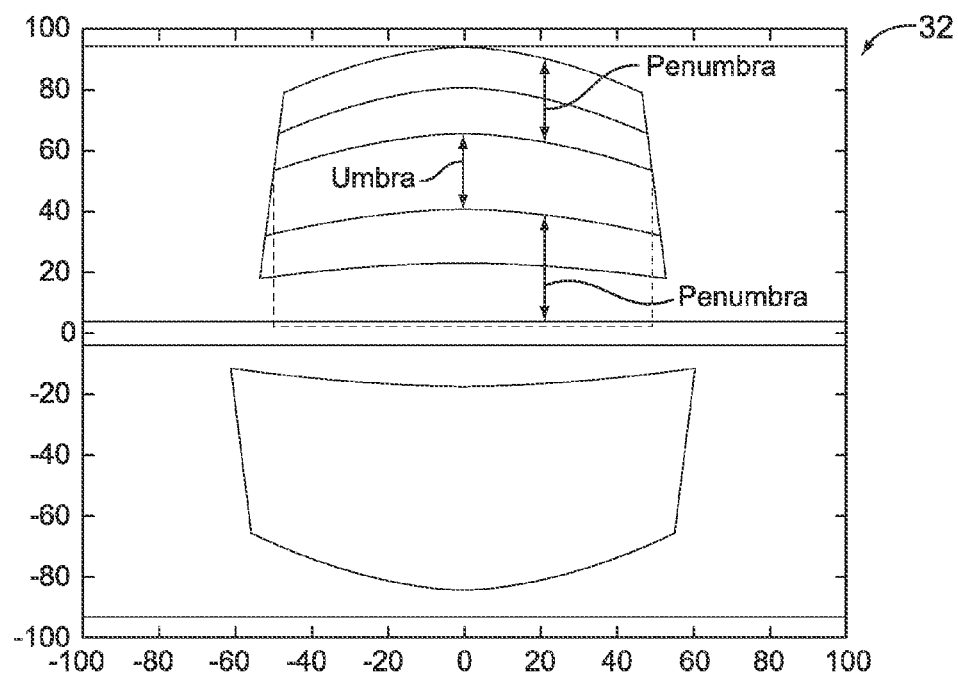
FIG. 9 is a graphical illustration of the umbra produced by an exemplary electron beam impinging on an exemplary target in accordance with an embodiment of the present invention.

FIG. 9 is a graphical illustration of the umbra produced by an exemplary x-ray radiation impinging on an exemplary detector during operation. More specifically, FIG. 9 illustrates the umbra formed on the detector 16 by the x-ray 40. The umbra is located approximately centrally on the detector 16. Moreover, the penumbras extend radially outward from the umbra on each side of the umbra. FIG. 9 therefore illustrates that the alignment of the detector with respect to the targets 20 and 26, and the detector rings 30 and 32 produce an umbra and penumbra that is sufficient to produce acceptable images during operation.

While the invention has been described in terms of various specific embodiments, those skilled in the art will recognize that the invention can be practiced with modification within the spirit and scope of the claims.

What is claimed is:

1. An x-ray radiation therapy and scanning system comprising:
   a therapy source adapted to deliver a predetermined dose of treatment x-ray radiation along a therapy axis to a patient positioned in a scan field;
   a stationary scanning source producing an electron beam;
   a detector positioned to partially circumscribe the scan field, the detector located on a first side of the therapy axis and offset from the therapy axis by a first non-zero angle; and
   a target arranged concentric with the detector and located opposite the detector across the scan field, the target located on an opposite second side of the therapy axis and positioned at a different second non-zero angle to the therapy axis such that when the electron beam impinges on the target the target transmits x-ray radiation through the scan field to the detector.

2. An x-ray radiation and therapy scanning system in accordance with claim 1 wherein the detector is divided into a pair of detector rings arranged adjacent to one another and separated by a gap extending at least partially about a circumference of the detector.

3. An x-ray radiation and therapy scanning system in accordance with claim 2 wherein the target comprises end portions circumferentially overlapping the detector and radially aligned with the detector rings, such that when the electron beam impinges on the target, the target transmits x-ray radiation through the gap across the scan field to an associated section of the detector.

4. An x-ray radiation and therapy scanning system in accordance with claim 1 further comprising a second target concentric with the detector and located opposite the detector across the scan field, the second target having end portions circumferentially overlapping the detector and radially aligned with a gap between the detector such that when the electron beam impinges on the second target the second target transmits x-ray radiation through the gap across the scan field to an associated section of the detector.

5. An x-ray radiation and therapy scanning system in accordance with claim 1 further comprising a second target concentric with the detector and located opposite the detector across the scan field, the second target having end portions circumferentially overlapping the detector and radially aligned with a gap between the detector, the target transmits x-ray radiation through the gap across the scan field to a first detector ring in the pair of detectors, the second target transmits x-ray radiation through the gap across the scan field to a second detector ring in the pair of detectors.

6. An x-ray radiation and therapy scanning system in accordance with claim 1 further comprising:
   a second stationary source producing a second electron beam; and
   a second target arranged concentric with the detector and located opposite the detector across the scan field, the second target having end portions circumferentially overlapping the detector and radially aligned with a gap between the detector such that when the electron beam produced by the second stationary source impinges on the second target, the second target transmits x-ray radiation through the gap across the scan field to an associated section of the detector.

7. An x-ray radiation and therapy scanning system in accordance with claim 1 further comprising:
   a second stationary source producing a second electron beam; and
   a second target arranged concentric with the detector and located opposite the detector across the scan field, the detectors comprising a pair of detector rings, the second target having end portions circumferentially overlapping the detector and radially aligned with a gap between the detector rings, the target transmits x-ray radiation through the gap across the scan field to a first detector ring in the pair of detectors, the second target transmits x-ray radiation through the gap across the scan field to a second detector ring in the pair of detectors.

8. An x-ray radiation and therapy scanning system in accordance with claim 1 further comprising a collimator positioned between the target and the detector.

9. An x-ray radiation and therapy scanning system in accordance with claim 1 wherein the detector comprises a x-ray radiation shield formed on a radially outer surface of the detector.

10. An x-ray radiation and therapy scanning system in accordance with claim 1 wherein the detector comprises a x-ray radiation shield formed on a radially outer surface of the detector, the x-ray radiation shield having a gap defined therethrough, a gap between the detector being substantially aligned with the gap defined through the shield.

11. An x-ray radiation and therapy scanning system in accordance with claim 1 further comprising a second target, the target having a diameter that is greater than a diameter of the second target.

12. A detector for an electron beam scanner, said detector comprising:
   a pair of detector rings, each the detector rings including a first detector portion and a second detector portion, the first detector portion having a first thickness and the second detector portion having a different second thickness, each of the first and second detector portions including
   a substrate having a first side and a second opposing side;
   a pixel array formed on the substrate first side; and
   an x-ray shield formed on the substrate opposing side.

13. A detector for an electron beam scanner, said detector comprising:
   a detector positioned to partially circumscribe a scan field, the detector divided into a pair of detector rings arranged adjacent to one another and separated by a gap extending at least partially about a circumference of the detector; and
   an x-ray shield, formed on a substrate of the detector, and extending at least partially through the gap.

14. The detector of claim 13, wherein the gap has a first width and the x-ray shield portion has a second width that is substantially the same as the width of the gap.

15. The detector of claim 13, wherein a size of the gap is selected based on a width of the detector rings.

16. An x-ray radiation therapy and scanning system comprising:
   a therapy source adapted to deliver a predetermined dose of treatment x-ray radiation along an axis to a patient positioned in a scan field;
   a stationary scanning source producing an electron beam;
   a pair of detector rings positioned to partially circumscribe the scan field; and
   a pair of targets arranged concentric with the detector and located opposite the detector across the scan field, the pair of targets at least partially overlapping the pair of detector rings, the pair of targets being positioned such that when the electron beam impinges on at least one of the targets, the target transmits x-rav radiation through the scan field to at least one detector in the pair of detector rings.

17. The x-ray radiation therapy and scanning system of claim 16 wherein the pair of targets are positioned at an angle θ to the axis such that when the electron beam impinges on the at least one target, the target transmits x-ray radiation through the scan field to the detector.

18. The x-ray radiation therapy and scanning system of claim 16 wherein the pair of targets are separated by a gap.

19. The x-ray radiation therapy and scanning system of claim 16 wherein the pair of targets comprise a pair of concentric targets extending approximately 220 degrees around the scan field.

* * * * *